ARTIFICIAL KIDNEY

Original Filed Sept. 29, 1966 5 Sheets-Sheet 1

Inventor:
JOSEF HOELTZENBEIN
By Richard J. Reilly
Attorney:

ARTIFICIAL KIDNEY

Original Filed Sept. 29, 1966 5 Sheets-Sheet 2

Inventor:
JOSEF HOELTZENBEIN
By Richard J. Reilly
Attorney.

ARTIFICIAL KIDNEY

Original Filed Sept. 29, 1966 5 Sheets-Sheet 3

Inventor:
JOSEF HOELTZENBEIN
By Richard J. Reilly
Attorney:

Inventor:
JOSEF HOELTZENBEIN
By Richard J. Reilly
Attorney:

INVENTOR.
JOSEF HOELTZBEIN
BY Richard J. Reilly

United States Patent Office

Re. 27,510
Reissued Oct. 24, 1972

27,510
ARTIFICIAL KIDNEY

Josef Hoeltzenbein, Muenster, Germany, assignor to Baxter Lab. Inc., Morton Grove, Ill.

Original No. 3,510,004, dated May 5, 1970, Ser. No. 720,812, Apr. 12, 1968, which is a continuation of Ser. No. 582,896, Sept. 29, 1966. Application for reissue Nov. 1, 1971, Ser. No. 194,278
Int. Cl. B01d *31/00*
U.S. Cl. 210—321 24 Claims

Matter enclosed in heavy brackets [ ] appears in the original patent but forms no part of this reissue specification; matter printed in italics indicates the additions made by reissue.

ABSTRACT OF THE DISCLOSURE

A dialysis tube for blood is coiled to form membraneous layers supported by a member having first and second strands arranged at angles from and projecting their length away from each other for forming flow channels for blood and dialyzing fluid.

This is a continuation of application Ser. No. 582,896, filed Sept. 29, 1966, now abandoned.

The new invention relates to improvements in an artificial kidney.

An artificial kidney is a dialysis apparatus through which blood is circulated and in which the blood is subjected to dialysis against a wash solution outside the living organism. As dialysis membrane, cellulose hydrate or cellulose acetate usually is employed, either in film form (film dialyzer) or in tubing form (tubing dialyzer). Dialysis apparatus of this kind must have a sufficiently great dialysis surface. Furthermore, the thickness of the blood layer must be slight since, on the one hand, for the dialysis process only the layers of washing liquid immediately adjacent to the membrane are effective and, on the other hand, the user then can dispense with prior filling of the apparatus with foreign blood which must then be removed and whose presence introduces certain dangers and drawbacks. The fact that a very thin layer of blood is necessarily used results in an undesirably high resistance to flow of the blood, so that inadmissibly high flow pressures are necessary, requiring a blood pump, which in turn, results in traumatizing the blood, with destruction of blood corpuscles. In the case of film dialyzers, this disadvantage is compensated for by arranging many small dialysis chambers in parallel, in order to diminish the resistance.

Apart from the mechanical problems of leak tightness and of blood supply, and the therefore frequently difficult assembly, apparatus of the known type usually can be sterilized only poorly. Clinically, therefore, the tubing dialyzers are given preference. Thus, according to the example of Bod von Garralts and of Inouye and Engelberg, a length of cellophane tubing together with a plastic braiding or with a tie band (coiling band) of transversely running cylindrical rods is wound with a spool around a core. The wash solution then flows transversely to the cellophane tubing, which is coiled in a horizontal plane and flattened by the tie band. Since the resistance to flow of the blood is intolerably high, spacer strips are interposed above and below the cellophane tubing to enable the tubing to unfold up to the thickness of the spacer strips, which thus determine the thickness of the blood layer.

In order to further diminish blood flow resistance, Kolff and Watschinger teach to coil a second cellophane tubing, connected in parallel, in a second tier around the same core, with a wider tie band. The wash solution then must first flow transversely past one tubing, thereby becoming partially depleted in washing ability by the time it reaches the second tubing. Parallel connections of additional tubings according to the above principle will thus reduce the efficiency all the more because the greater the number of tubing connected in tiers one above the other, the more the wash solution is depleted in passing each plane, or tier of tubing.

The present invention is advantageous for overcoming problems described above. According to one aspect of the present invention, at least two, preferably four, or more plastic film tubing capillary dialyzers, or membranes, are placed between novel porous tie bands to form an assembly of alternately layered tie bands and membranes with tie bands on the innermost and outermost layers. The membranes, or tubings, and tie bands are spirally wound around a core means in a spiral with the inlet of each tubing being staggered at substantially equal distance from inlets of adjacent tubings around the circumference of the core, and the outlet of each tubing being staggered at substantially equal distances from the outlets of adjacent tubings around the outer circumference of the spiral, the tubings being of about equal lengths.

Each tubing is in the form of a flattened cylinder and substantially ribbon-like in its flattened form. The tubing is known in the artificial kidney art. In a preferred embodiment of the invention the inlet end of each tubing is passed through an opening in the wall of the core means. A sufficient number of openings are provided in the core to accommodate the number of tubings used in the assembly. The openings are distributed at substantially equal distances from adjacent openings around the periphery of the core.

According to another aspect of the invention, it is further of advantage to pull the end of the dialysis tubing folded over a highly elastic terminal tube, together with the latter under strong friction, so as to be leakproof, through a conical bore of a confining rim, or sleeve. On the wrapping of the tubings and tie bands around the core, the beginning and end of each tubing are suitably arranged on the same geometrical generatrix of the spiral.

One novel feature of the improved artificial kidney thus consists in coiling two, or any desired number, of pieces of dialysis membrane tubing with two or any desired number of tie bands on a common core, in a plane, in the manner of a multiple-start spiral. By means of this novel arrangement of inlets and outlets of the membranes blood flow through the assembly is greatly increased, and as will be more full explained, fresh wash solution may simultaneously reach each membrane. Also because of the relatively short lengths of the multiple membranes of the present artificial kidney, compared to a single wrapped or parallelly wrapped dual membrane of the prior known assemblies, the dialysis effect is greatly enhanced.

The tie bands may consist of any inert suitable material, e.g. plastic, fiber glass, metal, in the form of netting, mesh or braidings, preferably with the addition of spacer strips. As support there also may be employed certain suitable cross-sectional strips, which may be fabricated of rubber, plastics or other materials which are inert in the presence of the washing solution and blood, with or without spaced strips, bands, threads or wires.

In practice of the invention, it is preferred to use tie bands which permit a dumbbell-shaped flattening of the e.g. cellophane, tubing. The use of such tie bands in multiple-start spirals is of special advantage with tubing dialyzers which permit a flattening of the cellophane. Especially preferred is a wire net having upper and lower support wires spaced apart at a distance substantially greater than the width of the flattened tubing membrane and hav- ıg a continuous strand of wire wound over the wires at an ngle of about 60°. In winding the wire strand, the strand ; spaced along the support wires at equal distances such ıat a suitable flow canal for wash solution will result, g. from about 1/16" to about 3/8" apart. The resulting et then has one set of strands of wire running parallel to ıch other one one side of the support wires and a corre- ɔonding set running parallel to each other on the other de of the wires. When two pieces of the resulting net are sed as tie bands with a tubing membrane interposed etween them, the opposing set of strands are pressed gainst each other and against the tubing to form channels ɔr flow of the wash solution. At the same time, the tubing, g. cellophane, bulges outwardly under the flow of blood owing through the tubing. At the crossing points of the rands, both sides of the cellophane tubing are compressed ı the shape of a point (or, in the case of addition of ɔacing strips, are brought close to one another to a efinite distance). Between the points, the cellophase tub- ıg may unfold depending on the prevailing pressure and ıe elasticity of the cellophane. Depending on the mesh ze formed by the spacing of the wound strand, various zed, bag-shaped pouches of the cellophane tubing are ɔrmed, within which the blood flows, and between which ıe wash solution flows. With increasing mesh size, the ctension of the cellophane tubing is ultimately limited, y the fact, among others, that the bag-shaped pouches of eighboring layers of the cellophane tubing at first touch : a point, and at greater pressure finally along a surface. ı this way there is a maximum limit for the blood volume resent in the tubing at any fixed pressure. With a suffi- ently large mesh size one can dispense with the use of ɔacer strips.

The use of such nettings of wires crossing one another ɔr tie bands in an artificial kidney is regarded as novel. he use of such tie bands are deemed advantageous also ɔr use in the case of other, previously known designs of rtificial kidneys which include the use of porous tie bands The leak tightness of each end of the cellophane tubing ıembrane at the transition to the inlet and the outlet of ıe blood tubes is effected by inserting an elastic, e.g. syn- ıetic rubber or gum rubber, tube into each end of the ıembrane and folding the membrane, i.e. the cellophane ıbing, around the elastic tube. In the case of the inlet ıd, the folded end of the membrane and the blood tube e then passed through the narrow end, i.e. the end ıving the smallest inner diameter of a conical bore in ıe core or in a confining rim on the inner periphery of the ɔre, or preferably, through a detachable plastic funnel- ıaped conical sleeve. The bore must have a smaller inner ameter than the outer diameter of the resilient blood ıbe so that it will restrict the inserted tubings. The bore ıould be located in a smoothly polished material, e.g. ɔlytetrafluoroethylene (Teflon), polyethylene, polyvinyl- ıloride, or other synthetic plastic, the first being pre- ɜrred, so that the holding friction of the cellophane tubing ı be pulled through against the synthetic rubber or gum ıbber is very much greater than the friction between the ɔre wall and the rubber and cellophane. In the case of ıe outlet end, the membrane and tubing are fastened milarly to the outer casing of the assembly.

The improved artificial kidney is represented in the rawing in an illustrative but preferred embodiment.

Figure 1:
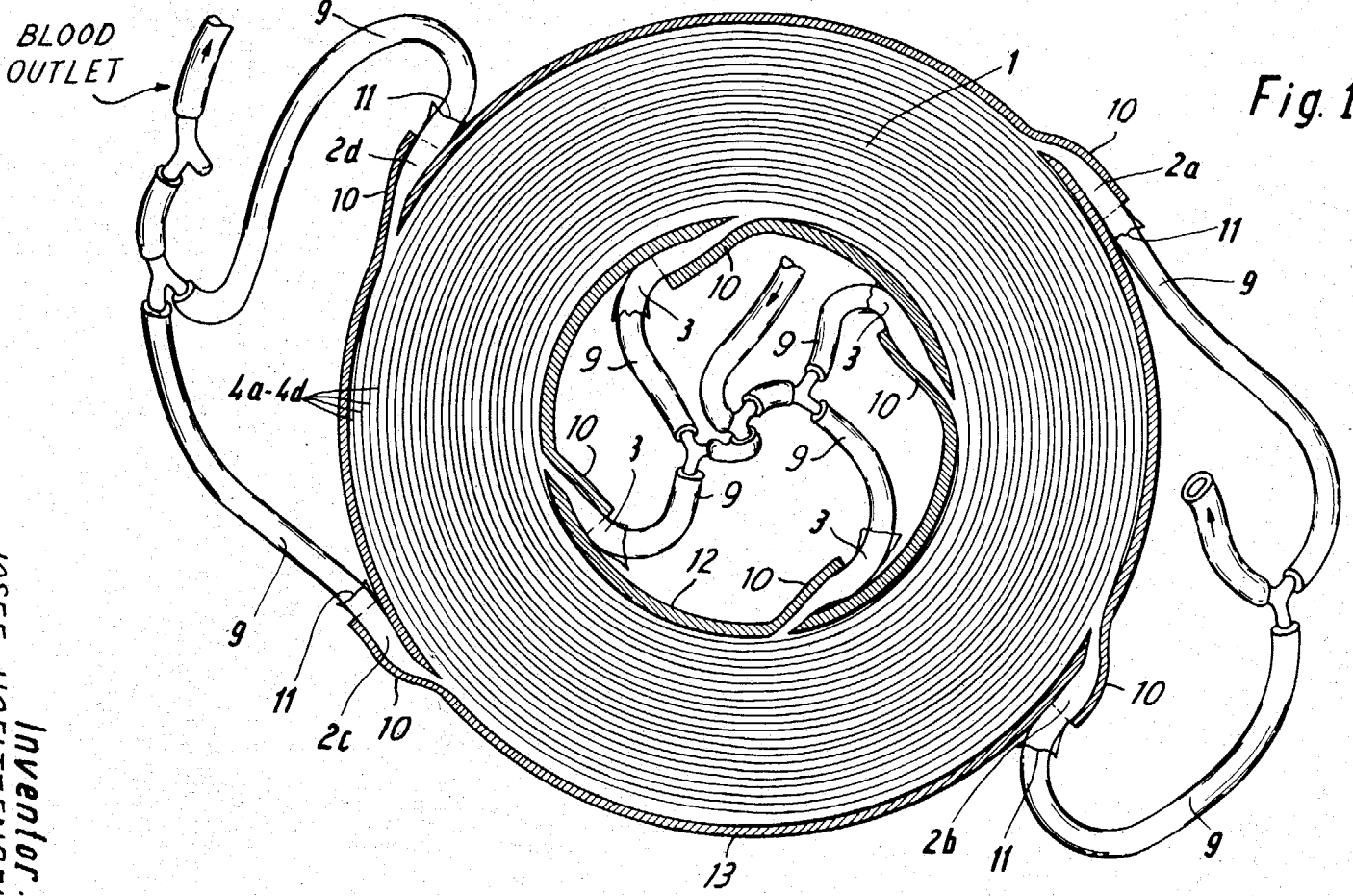
FIG. 1 is a central horizontal cross section through the rtificial kidney assembly in operating condition.
Figure 2:
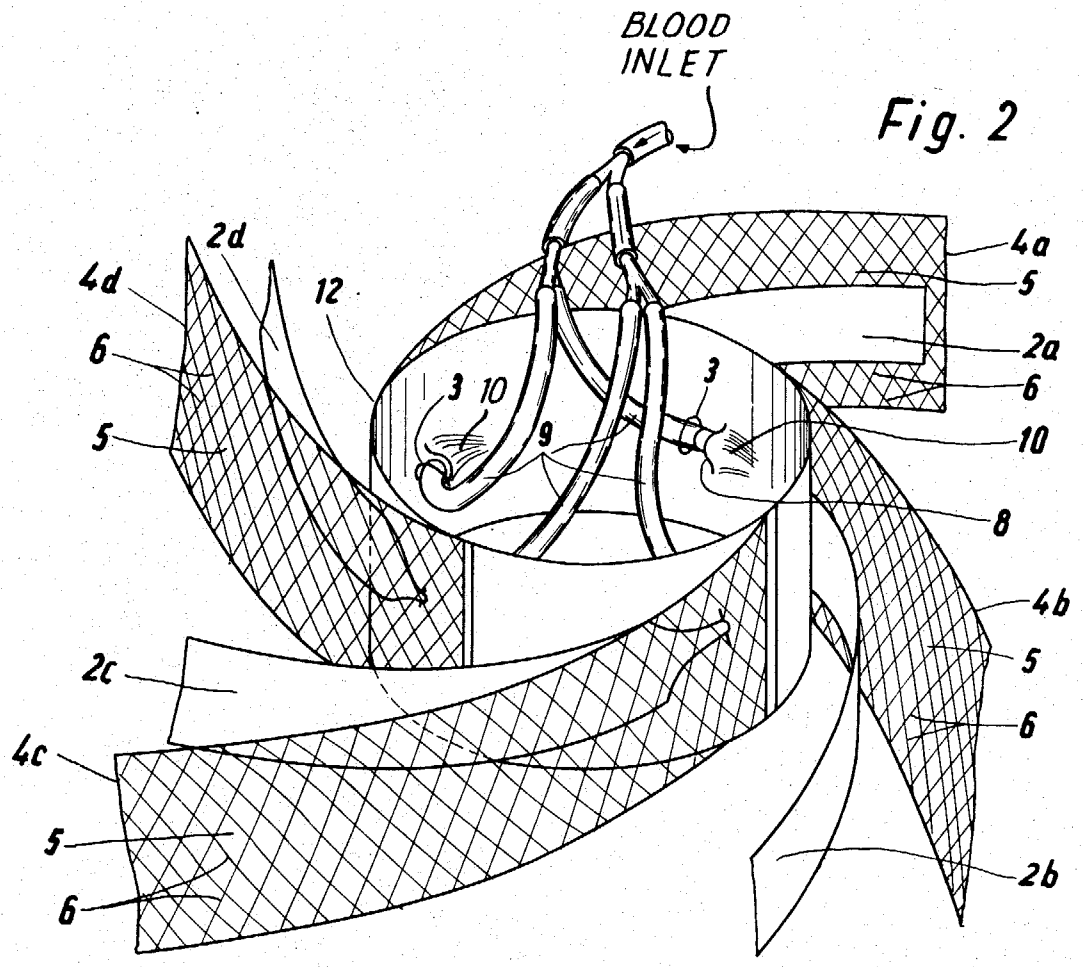
FIG. 2 is a diagram of the kidney in the first stage of s novel manner of coiling, in schematic representation.

In detail, one recognizes that in a plane geometrical spiral 1 in the example of the embodiment there are coiled about a core 12 four tubings, 2a to 2d, one upon another. The beginning inlets 3 and ends (outlets) 11 of the tubings 2a to 2d are substantially uniformly staggered along the circumference of the spiral 1; in the example of the embodiment by 90°. Between the tubings 2a to 2d there are coiled porous tie bands 4a to 4d, in such a way that each tube surface is tightly and statistically homogeneously bordered by two tie bands.

The tie bands 4a to 4d consist of nettings level in a plane, of crossing strand wires 6. In use, these cause formation of statistically homogeneously distributed pouches 7 of the tubings 2a to 2d during the dialysis process.

Figure 3:
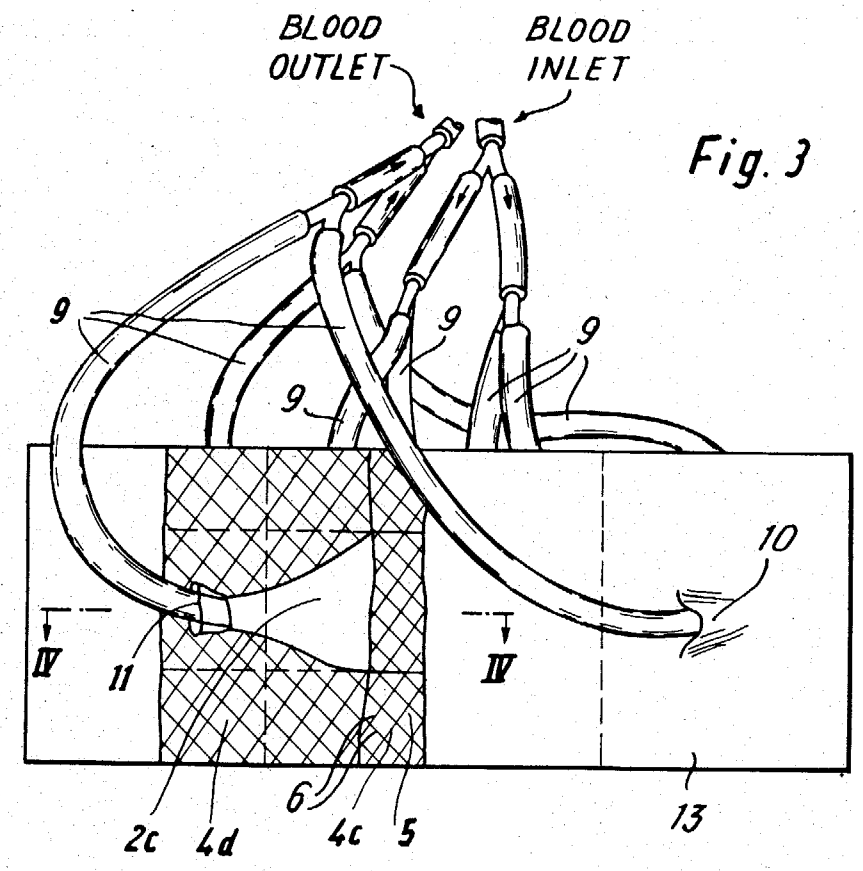
FIG. 3 is a side view of the artificial kidney from the utside, with individual parts in section.

The ends 11 of the dialysis tubings 2a to 2d are, as shown especially in FIG. 3, folded around a highly elastic terminal tube 9 and are pulled together with the latter under strong friction, so as to be leakproof, through a conical bore 8 of a confining rim 10 in the outer casing 13 of the artificial kidney assembly. This arrangement of the beginnings and the ends of the tubings 2a to 2d is located advantageously on a uniformly divided circumference of a circle. In the example of the embodiment, which uses four tubings, the beginnings and ends of the latter are staggered each by 90° on the tubing circumference; if three tubings were present, one would obtain a distance of 120°. With the use of more than four tubings the circle would be uniformly divided correspondingly. Expressed geometrically, the beginning and end of each tubing 2a to 2d therefore are located on the generatrix of the spiral 1.

Figures 4, 5:
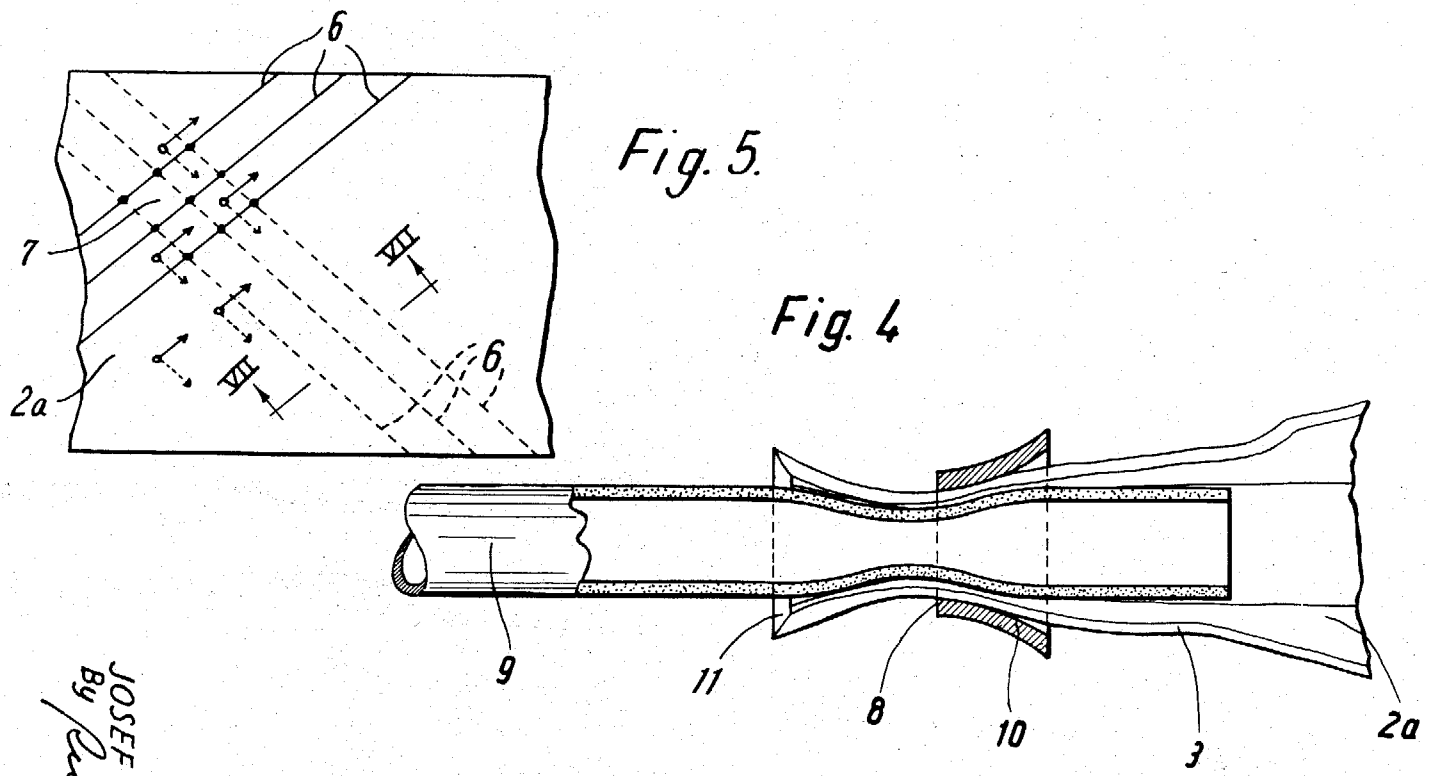
FIG. 4 shows, greatly magnified, a detail of FIG. 3 in ıe longitudinal section IV—IV.
FIG. 5 shows schematically the flow directions of the ash solution through the channels formed by two tie ands with the membrane interposed between them.

In FIG. 5, the solid arrows indicate the direction of flow of the wash solution on the front surface of the outside of the membrane and the dashed arrows indicate the direction of flow of the wash solution on the back surface of the outside of the membrane. The area within the intersections of pairs of the upper and lower wires 6 is filled by the membranes 2a under blood flow pressure to form a pouch 7. Each surface of the pouch 7 is thus washed by wash solution flowing as indicated by the arrows. As may be seen in FIG. 5, when the strands of wire on the front side of the netting are positioned at 60°, the strands of wire on the back, or opposite side are at an angle of 120°, viewed along the arrows. A multiplicity of four-sided pouches 7 thus is formed.

Figure 6:
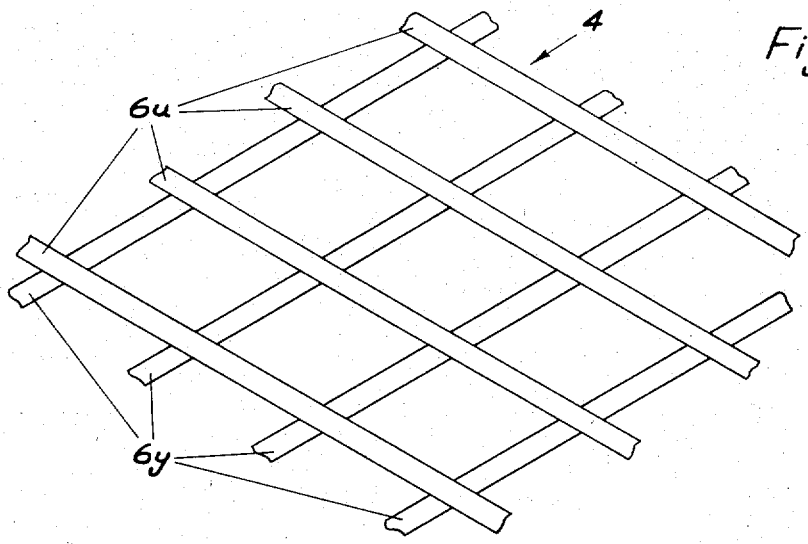
FIG. 6 is an enlarged fragment of a plan view of a tie band or membrane support member embodying one aspect of the invention.

FIG. 6 illustrates that strands or wires 6, of a tie band or membrane support member 4 which is typical of tie bands 4a, 4b, 4c and 4d, are parallel in a plane in a first or upper set 6u, and parallel in a plane in a second or lower set 6y. Membrane support member 4 may be of plastic fabrication with its strands 6u arranged at an angle to the strands 6y. The thickness of the strands of each set project their lengths from opposite sides of an imaginary plane P (shown in phantom line in FIG. 7); and strands 6y are secured, for example, by fusion to strands 6u at their intersecting angle forming points. Strands 6u, which are of uniform thickness, define a first surface of support member 4; and strands 6y are also of uniform thickness and define another surface of said support member opposed to the first surface. In consequence of the foregoing, each support member 4 is comprised of two opposed pair of channel defining strands which enable formation in the dialyzers engaged thereby of a pair of corresponding channel sets which are angularly disposed. One set of channels 20u will be formed by strands 6u while another set of channels 20y will be formed by reason of strands 6y.

Figure 7:
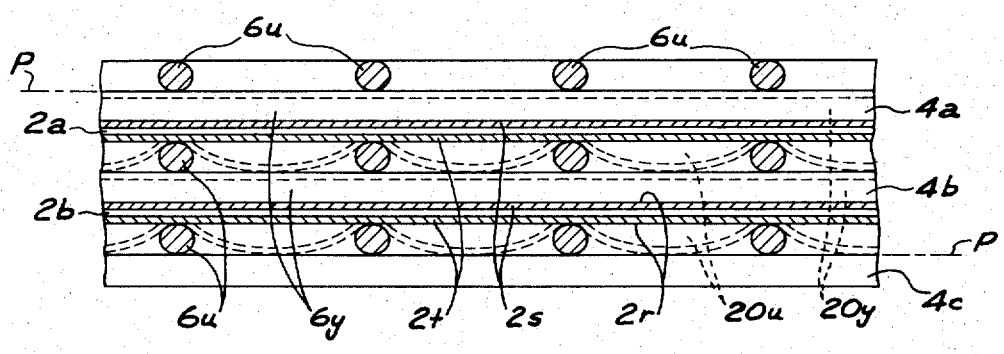
FIG. 7 is an enlarged detail view of a support member used in this invention.

In FIG. 7, three support members 4a, 4b and 4c are shown with tubular dialyzers 2a and 2b disposed therebetween. Each of said tubular dialyzers comprises a pair of substantially parallel diffusion sections 2s and 2t. These sections have inner faces arranged for passing therebetween a first fluid (blood). Sections 2a and 2t also have opposed outer surfaces 2r supportively disposed against adjacent of support members 4 and adapted for engaging a second (dialyzing) fluid for material exchange across said diffusion sections. Under pressure of fluid in dialyzer 2a diffusion section 2t will be forced from its solid line position of FIG. 7 between strands 6u to form therebetween elongated channels 20u (shown in dotted lines) in said dialyzer. At the same time section 2s will be forced into a plurality of parallel channels 20y (shown in dotted line) between strands 6y. The channels 20u and 20y thus formed will be disposed in a pair of parallel sets at an angle, one to the other, and with the channel walls of each set being of uniform height.

The foregoing arrangement minimizes channelling due to differential resistance within diffusion apparatus, such as an artificial kidney, by providing uniform fluid pathways. Such is not experienced when a support member is woven. That is to say improved results obtain because in each support member 4 strands 6y are disposed in a plane from which strands 6u are absent while strands 6u are disposed in a plane from which strands 6y are absent. Accordingly, the flow paths defined by channels 20y and 20u will be free from crossing impediment to flow.

The improved articial kidney of the invention is sterilized and used in a known manner. For example, the sterilized artificial kidney is installed in a sterilized sealable dialyzer chamber having openings through which the inlet and outlet blood flow tubes pass by means of leakproof connectors. For ease of use the inlet of each blood flow tubing is joined with the other inlets to a single main inlet connection which leads to a line coming from the patient. The outlets of the blood flow tubes are similarly joined to a main outlet line going back to the patient. Dialyzer wash solution of known composition is circulated through the chamber through suitable openings. The flow of wash solution in the chamber is arranged so that in passing through the chamber the solution is forced through the artificial kidney through the channels formed by the wires 6 of netting 5 of the tie bands 4a–4d. The solution washes over the outer surfaces of the pouches 7 formed by the membranes and tie bands, removing the waste products dialyzed through the membranes from the blood passing through the membrane tubings. The blood to be purified by the dialyzer solution is circulated through the blood flow tubes from patient's artery and is discharged back to a vein by the force of the patient's own blood pressure, no pump usually being necessary.

In one embodment of the improved artificial kidney, the wire distance was approximately 5 mm. and the wire was 1 mm. thick. The wires were run at a 60° angle. Even when the netting was pulled tightly over the cellophane, blood passed through readily, and spacers were not necessary.

Various lengths and numbers of tubing can be used. Four coils of 4 meters of 36/32" Visking casing were found to contain a total of between 450 and 490 ml. and to provide a surface area of 14,400 cm.$^2$.

A clearance of sodium ions of between 140 to 150 ml./min. was obtained at a blood flow rate of 200 ml./min. A maximum clearance of 220 ml. was reached at a flow of 400 ml./min., in vitro.

The blood flow resistance of the improved artificial kidney is low. When tested with water, a waterhead of 100 cm., that is, roughly 75 mm. Hg, produced a flow of 330 ml./min. The coils are disposable.

In a clinical test, in one patient with a systolic blood pressure of 140 mm. Hg, a blood flow of 180 ml. was obtained without a pump.

Many different embodiments of this invention can be made without departing from the scope and spirit of it, as will be obvious to those skilled in the art, and it is to be understood that the invention includes all such embodiments and is not limited by the above description.

What is claimed is:

1. On an artificial kidney using as a dialyzer a flattened tubing of plastic film coiled spirally and embedded between foraminous bands of netting, the improvement which comprises a spiral assembly of dialyzer tubing positioned between said bands and positioned about a core, in which said band consists of a netting of crossing strands comprising an upper set and a lower set of parallel strands, level in a plane, and each set of crossing strands supporting and lying against opposing sides of said dialyzer tubing and defining an angle to each other, which in use during dialysis in combination with said dialyzer tubing causes a formation of statistically homogeneously distributed interconnected pouches along said dialysis tubing to define flow channels.

2. The artificial kidney according to claim 1 wherein said angle is about 60°.

3. A combination according to claim 1 characterized in that the parallel support strands of said upper set are of uniform thickness and define one surface of said netting, the parallel strands of said lower set being of uniform thickness and defining a second surface of said netting, said second and first surfaces being in opposed relationship and enabling formation of sets of parallel channels in said dialyzer tubing.

4. The artificial kidney of claim 1 in which the only spacer means is said netting.

5. The artificial kidney of claim 1 in which said netting is made of plastic.

6. The artificial kidney of claim 1 in which said tubing is made of cellophane.

7. The artificial kidney of claim 1 in which each set of strands defines an angle with respect to the planes defining the sides of said spiral assembly.

8. An artificial kidney according to claim 1 having a plurality of said flattened dialyzer tubings wound in a coil wherein the beginning and end of each dialyzer tubing are located on the same generatrix of the spiral.

9. A combination according to claim 1 in which the upper and lower sets of strands are secured together at intersecting angle forming points.

10. An artificial kidney according to claim 1 wherein each end of a dialyzer tubing has been folded around an elastic terminal tube and has been pulled together with the latter under strong friction so as to be leakproof through the bore of a conical confining rim.

11. An artificial kidney according to claim 10 wherein a plastic funnel-shaped sleeve tapered inwardly in the direction of a dialyzer tubing and having smooth outwardly arched walls, serves as means for attaining leak tightness of the connection to the elastic terminal.

12. In an artificial kidney having *a flattened tubular membrane defining* a pair of opposed dialysis membrane sections with facing inner surfaces arranged for passing therebetween a first fluid for material exchange with a second fluid disposed in contact with the other surfaces of said membrane sections, the combination comprising: an upper set of parallel channel defining strands in a first plane and supportingly disposed against the outer surface of one of said membrane sections; and a lower set of parallel channel defining strands in a second plane distinct from said first plane, said lower set of strands defining an angle with respect to said upper set of strands and supportingly disposed against the outer surface of the other of said membrane sections; whereby two sets of flow channels, each set of flow channels defining an angle with the other set, will be formed in said membrane sections under fluid pressure therebetween.

13. A combination according to claim 12 in which the upper and lower strands are spaced from each other by a distance equal to at least the thickness of said sections.

14. The combination according to claim 12 in which said membrane sections comprise sides of flattened tubing.

15. The combination according to claim 14 in which ıid angle between the strands of the upper and lower sets ; about 60°.

16. The combination according to claim 14 in which ıe strands of said upper and lower sets and the memrane sections are disposed in a spiral connfiguration, each f said sets of strands and sections occupying a different ɔiral plane.

17. The combination according to claim 12 in which ıid upper and lower sets of strands comprise plastic netng disposed in face to face contact with said membrane ɛctions.

18. The artificial kidney of claim 17 in which the only ɔacer means is said netting.

19. An artificial kidney comprising (a) a core means;

(b) a multiplicity of dialyzer membrane tubings spirally wound around said core means in a plane spiral with the inlet of each tubing positioned at substantially equal distances from inlets of adjacent tubings around the circumference of the core, and the outlet of each tubing positioned at substantially equal distances from outlets of adjacent tubings around the outer circumference of the spiral, said tubings being of about equal lengths;

(c) a corresponding multiplicity of tie bands positioned to separate said tubular membranes from each other and spirally wound with said membranes around said core to form a tightly wound spiral coil, each tie band being at least as long as a tubing;

(d) a casing for the peripheral surface of said spiral coil;

(e) leakproof connector means for said inlets positioned in openings passing through the wall of said core means from the outer periphery to the inner periphery thereof; and (f) leakproof connector means for said outlets positioned in openings passing through the wall of said casing from the inner periphery to the outer periphery thereof.

20. The artificial kidney according to claim 19 wherein ıid leakproof connector means each comprises a conical ore with the smallest diameter of the bore on the memrane tubing side of the connector means.

21. The artificial kidney according to claim 19 wherein ıe leakproof connector means is a detachable funnelıaped conical sleeve.

22. The artificial kidney of claim 1 containing a pluality of separate bands of netting.

*23. In an artificial kidney having a spirally arranged, attened tubular membrane defining a pair of opposed ialysis membrane sections with facing inner surfaces, nd means for passing blood therebetween within said ıbular membrane, for material exchange with wash solu-on disposed in contact with the outer surfaces of said ıembrane sections, the combination comprising: memrane support netting which consists of an upper set of parallel, channel-defining strands in a first spiral plane and supportingly disposed against the outer surface of one of said membrane sections; and a lower set of parallel channel defining strands in a second spiral plane distinct from said first plane, said lower set of strands defining an angle with respect to said upper set of strands, and supportingly disposed against the outer surface of the other of said membrane sections; whereby two sets of flow channels, each set of flow channels defining an angle with the other set, will be formed in said membrane sections under fluid pressure therebetween.*

*24. In an artificial kidney using a dialyzer a flattened tubing of plastic film coiled spirally and embedded between foraminous bands of netting, the improvement which comprises a spiral assembly of dialyzer tubing positioned between said bands and positioned about a core, in which said band consists of a netting of crossing strands consisting of an upper set and a lower set of parallel strands, level in a plane, and each set of crossing strands supporting and lying against opposing sides of said dialyzer tubing and defining an angle to each other, which in use during dialysis in combination with said dialyzer tubing causes a formation of statistically homogeneously distributed interconnected pouches along said dialysis tubing to define flow channels.*

References Cited

The following references, cited by the Examiner, are of record in the patented file of this patent or the original patent.

UNITED STATES PATENTS

| | | | |
|---|---|---|---|
| 2,982,416 | 5/1961 | Bell | 210—321 |
| 3,077,268 | 2/1963 | Gobel et al. | 210—321 |
| 3,342,719 | 9/1967 | Chen et al. | 204—301 |
| 3,489,647 | 1/1970 | Kolobow | 195—1.8 |

FOREIGN PATENTS

| | | | |
|---|---|---|---|
| 1,300,140 | 6/1962 | France | 210—321 |

OTHER REFERENCES

Kolff et al.: "Further Development of Coil Kidney," J. Lab. & Clinical Med., June 1956, pp. 969–977.

Kolobow et al.: "A New Dynamic Disposal Artificial Kidney," vol. X, Trans. Amer. Soc. Artif. Int. Organs, 1964, pp. 116–120.

Kolobow et al.: "Dialysate Capacity Augmentation at Ultra-Low Flow Rates With Activated Carbon Slurry," from vol. XII Trans, Amer. Soc. Artif. Int. Organs, 1966, pp. 1–6.

Proceedings—Conference on Hemodialysis, N.I.H., Nov. 9–10, 1964, pp. 78–94.

FRANK A. SPEAR, Jr., Primary Examiner

U.S. Cl. X.R.

210—494, 541